United States Patent [19]

Lipham et al.

[11] Patent Number: 4,880,632
[45] Date of Patent: Nov. 14, 1989

[54] PREVENTION OF FESCUE TOXICOSIS

[75] Inventors: Luke B. Lipham; John A. Stuedemann; Frederick N. Thompson, Jr., all of Athens, Ga.

[73] Assignees: The United States of America, Washington, D.C.; University of Georgia Research Roundation, Inc., Athens, Ga.

[21] Appl. No.: 93,951

[22] Filed: Sep. 8, 1987

[51] Int. Cl.$^4$ ..................... A61K 9/26; A61K 31/165
[52] U.S. Cl. .................................. 424/425; 424/442; 424/486; 424/78; 424/422; 514/619; 514/617
[58] Field of Search ............... 424/442, 423, 422, 425, 424/486, 443, 78; 514/619, 428

[56] References Cited

U.S. PATENT DOCUMENTS

| | | | |
|---|---|---|---|
| 4,536,386 | 8/1985 | Keenan | 514/619 |
| 4,605,670 | 8/1986 | Saito et al. | 514/619 |
| 4,711,782 | 12/1987 | Okada et al. | 514/963 |
| 4,755,519 | 7/1988 | Dougherty et al. | 514/276 |

OTHER PUBLICATIONS

Lipham et al., Proc. Soc. Exper. Biol. Med. 184, 250–255 (1987).
Robbins et al., Appl. Environ. Microbiol. 35, 576–581 (1977).
Stuedemann et al., J. Anim. Sci. 63 (Suppl. 1), 290–291 (1986).
Stuedemann et al., Am J. Vet. Res. 46, 1990–1995 (1985).
Monroe et al., J. Anim. Sci. (Suppl. 1), 50 (1987).
Henson et al., Domestic Animal Endocrinology 4 (1), 7–15 (1987).,
Bolt et al., J. Anim. Sci. 115, 48 (1982).
Hurley et al., J. Anim. Sci. 51 (2), 374–379 (1981).
Gorewit, J. Endocrinol. Invest. 4, 135–139 (1981).
Meltzer et al., Life Sci. 19, 1073–1078 (1976).
Lipham et al., Am. J. Vet. Res. 47 (5), 1089–1091 (May 1986).
"Pharmacologic Modulation of Serum Concentrations: Implications for Antagonism of Fescue Toxicosis in Cattle" by Luke Blair Lipham, A Dissertation presented to Graduate Faculty of the University of Georgia, Athens, Ga. (1988), pp. 1–64.

Primary Examiner—Joseph L. Schofer
Assistant Examiner—Pili Curtis
Attorney, Agent, or Firm—Kilpatrick & Cody

[57] ABSTRACT

A method, and compositions, for use in the prevention and treatment of fescue toxicosis in animals, especially cattle, sheep and horses, comprising administering to the animals a dopamine antagonist which does not cause adverse psychological or neurological effects. Useful dopamine antagonists are those specific for $D_2$ receptors including metoclopramide, sulpiride, tiapride, alizapride and other substituted benzamides. The preferred compound is metoclopramide, a substituted benzamide having the formula 4-amino-5 chloro-N-[2-(diethylamino)ethyl]-2-methoxy benzamide monohydrochloride monohydrate. The correct dosage can be determined from the combination of the behavioral response of the animal to the compound and by measuring the serum prolactin levels over time.

In the preferred method, the compound is administered to the animals orally, using capsules, timed or slow release boluses, or as an additive in a salt, mineral, protein or energy block or animal feed, or as an implant.

8 Claims, 4 Drawing Sheets

PREVENTION OF FESCUE TOXICOSIS

This application is in the area of veterinary medicine and particularly a method for the prevention and treatment of fescue toxicosis.

BACKGROUND OF THE INVENTION

Tall fescue, grown on over 35 million acres, is the most widely spread pasture grass in humid areas of the eastern U.S.A. and, to a limited extent, in the northwestern U.S.A. It is also commonly used for vegetative cover on highway banks, parks, playgrounds, home lawns, and waterways.

There are many reasons for its popularity: ease and wide range of establishment, wide range of adaptation, long grazing season, tolerance to abuse, pest resistance, good seed production, and excellent appearance when used for non-forage purposes. Tolerance of tall fescue to adverse climate, soil, and management conditions has aroused new interest and stimulated breeding and selection programs in countries such as France, Japan, Australia, New Zealand, and the USSR.

With increased use of tall fescue in pastures, beginning in the 1940's, there soon were disturbing reports of poor animal performance and visible disorders. This was puzzling since digestible dry matter, crude protein, amino acid, and mineral content suggested that well managed tall fescue should give good animal performance. However, in grazing studies, beef steer gains were low, usually only about 1 lb/day for the season. Gains on tall fescue were substantially lower than on orchardgrass. With beef cattle, calf gains and cow conception rates were substantially lower on tall fescue than on tall fescue-clover.

There are three principle symptoms of fescue toxicosis. The most dramatic visible symptom occurring on cattle grazing tall fescue is "fescue foot," a gangrenous condition of feet and/or tails. This syndrome appears to be related to lower ambient temperature and is much more widespread in northern than in southern parts of the tall fescue-growing region.

The second syndrome of cattle grazing tall fescue is bovine fat necrosis, which is characterized by hard fat masses and abdominal fat tissue deposits, often in adipose tissue surrounding intestines, causing poor digestion and calving problems. Originally associated with heavy applications of broiler litter to tall fescue pastures, it was later found the syndrome could occur with high nitrogen fertilizer.

The third and most common syndrome associated with tall fescue is "summer slump" or summer fescue toxicosis because of accentuated poor animal appearance and performance in summer. It is characterized by poor animal gains, intolerance to heat, excessive salivation, rough hair coat, elevated body temperature, nervousness, dramatically reduced weaning weights, lower milk production of both beef and dairy cows, and reduced pregnancy rate. In contrast to fescue foot and fat necrosis syndromes, summer fescue toxicosis is common and widespread throughout tall fescue-growing regions.

In 1973, J. D. Robbins, a chemist at the USDA Russell Research Center in Athens, Georgia, fungal physiologist C. W. Bacon and medicinal organic chemist J. K. Porter hypothesized that a fungus might be involved in the toxic syndrome. This hypothesis was based on work in New Zealand which showed tall fescue was subject to infection by an endophyte. Sampling of pastures in Georgia and four other states led them to postulate in *Appl. Environ. Microbiol.* 35, 576–581 (1977), that the fungal endophyte *Epichloe typhina* was associated with fescue toxicosis in cattle. The endophyte was later reclassified as *Acremonium coenophialum*. They predicted the endophyte was seed transmitted and would die if seed were stored for 1 to 2 years.

Subsequent grazing trials did not prove a cause and effect relationship, but did confirm that the fungal endophyte was associated with fescue toxicosis and that excellent animal performance could be achieved on low-endophyte tall fescue.

Since the early studies that associated the endophyte with reduced animal performance, considerable research has been devoted to confirming and documenting the extent of detrimental effects of endophyte-infected tall fescue. Generally, steer ADG has been increased from 30 to over 100% by shifting from high- to low- endophyte pastures. Gain per acre has been increased to a lesser extent, probably a result of lower intake and resulting higher carrying capacity of high-endophyte pastures. Intake is 10 to 50% higher on low- than on high-endophyte hay or seed. Results of studies appear to indicate a linear relationship between endophyte level and reduction in steer gains. Stuedemann et al., *J. Anim. Sci.*, 63 (Suppl.1), 290–291 (1986) observed a significant linear relationship between ADG and average percent endophyte, indicating that for each 10% increase in endophyte frequency, there was a 0.12 lb depression in ADG.

Cattle grazing toxic tall fescue have a tendency to wallow in mud, particularly during hot times of the day, as well as spend much less time grazing than cattle on other grasses. When moved from high- to low-endophyte tall fescue, steers grazed an amount of time similar to those remaining on the high-endophyte fescue for at least 26 days following exchange, indicating that grazing high-endophyte tall fescue has a residual effect.

Although intake reduction could account for much of the difference in animal performance on low- and high-endophyte tall fescue, the decreased grazing behavior even after the cattle are removed from the high endophyte fescue and systemic effects, including fescue foot and bovine fat necrosis, appeared to be a result of a toxic substance(s) present in the endophyte infested fescue. Several clinical signs of tall fescue toxicosis including increased body temperature, reduced performance, and rough hair coat could be caused by heat stress or administration of a pyrogenic substance. Inhibition of rumen microflora activity, particularly cellulolytic activity, by perloline and loline alkaloids, suggested alkaloids might be responsible.

A great deal of research has now been done on various alkaloids present in toxic fescue. Although a causal relationship with fescue toxicosis has not been demonstrated, steers grazing G1-307 (an experimental, high-endophyte line with low perloline concentration and high N-acetyl plus N-formyl loline alkaloid concentration) exhibit the greatest signs of summer fescue toxicosis and have the lowest serum cholesterol concentrations, as reported by Stuedemann et al., in *Am. J. Vet. Res.* 46, 1990-1995 (1985). It therefore appears that toxic tall fescue influences lipid metabolism, possibly due to action by alkaloid(s) present in the grass.

Few controlled grazing studies have been conducted with sheep to determine the effect of endophyte infection on animal performance. A number of studies have utilized sheep as models in controlled metabolism or physiology studies. Generally, these studies indicate responses similar to those found with cattle, though there may be magnitude differences.

Controlled studies have not been conducted with horses, but tall fescue, presumably endophyte-infected, has been associated with reproductive and agalactia problems in mares. Monroe et al., *J. Anim. Sci.* (Suppl.1): 50 (1987), studied mares grazing endophyte-infected and endophyte-free tall fescue with and without selenium. Mares grazing infected fescue showed a greater incidence of agalactia (88%) and retained placentas (75%). There have been other case reports of high foal mortality, low conception rates and agalactia in mares grazing on fescue infected with the endophyte.

At the present time, there are few options for preventing or treating fescue toxicosis. A recent estimate blames fescue toxicosis for losses by the livestock industry of between 200 million and one billion dollars per year. With high levels of endophyte infection, pasture replacement may be the preferred method for preventing fescue toxicosis. It is more difficult to assess the cost effectiveness of renovating pasture having intermediate levels of infection by the endophyte. It would be preferable to have a practical means for treating animals grazing or ingesting infected fescue with the flexibility of addressing the problem on an individual basis.

It is therefore an object of the present invention to provide a method for treating fescue toxicosis in grazing animals, especially cattle, sheep and horses.

It is another object of the present invention to provide a commercially useful drug and means for administering the drug which prevents fescue toxicosis in animals grazing on infected pastures or ingesting harvested infected fescue.

It is a further object of the present invention to provide a method and compositions for preventing fescue toxicosis in grazing animals which do not have serious side effects or create problems with the handling or end utilization of the animals.

SUMMARY OF THE INVENTION

A method, and compositions, for use in the prevention and treatment of fescue toxicosis in grazing animals, especially cattle, sheep and horses, comprising administering to the animals a dopamine antagonist which does not cause behavioral modifications. The most preferred compound is metoclopramide, a substituted benzamide having the formula 4-amino-5 chloro-N-[2-(diethylamino)ethyl]-2-methoxy benzamide monohydrochloride monohydrate. Substituted benzamides including sulpiride, tiapride, alizapride, and other $D_2$ specific dopamine antagonists should also be useful. Care must be taken in the selection of the dopamine antagonist to avoid administration of compounds having psychotropic, neuroleptic or adverse neurological actions. The correct dosage can be determined from both the behavioral response of the animal to the compound and measurements of the serum prolactin levels, and will be expected to vary according to the animals being treated, the method of administration and the extent of endophyte infection.

In the preferred method, the compound is administered to the animals orally, using capsules, timed or slow release boluses, or as an additive in a salt, trace mineral, molasses or protein block or animal feed, or as an implant. An effective dosage of metoclopramide is 15 mg/kg three times weekly when administered orally by capsule.

DETAILED DESCRIPTION OF THE INVENTION

Figure 1:
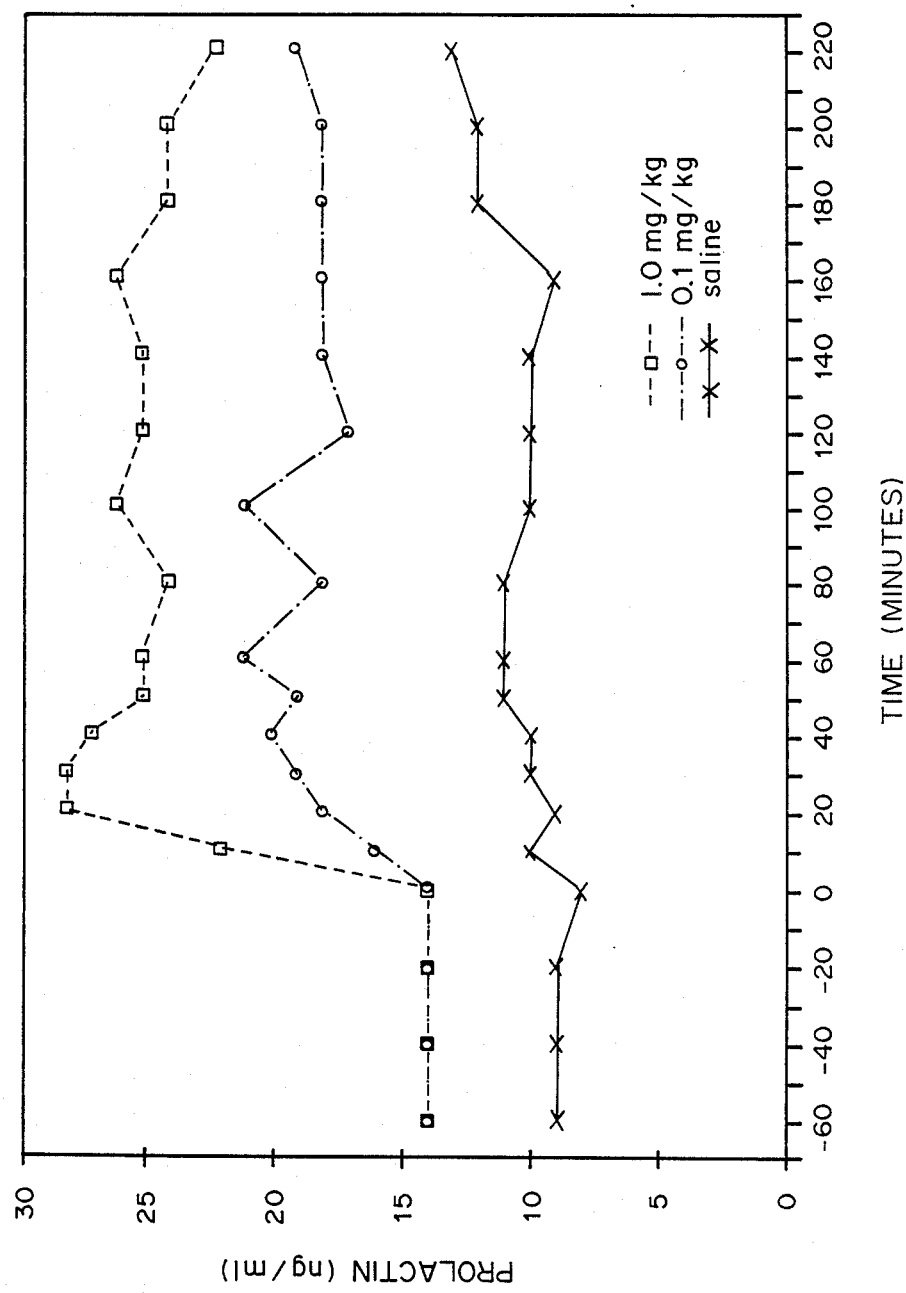
FIG. 1 is a graph of the effect of i.v. administration of metoclopramide (0.1 and 1.0 mg/kg) on serum prolactin levels (ng/ml) over time (min) in cattle grazing on bermuda grass pasture.

Fescue toxicosis is a condition occurring in animals grazing fescue forage infected with the fungus *Acremonium coenophialum*. This fungus is commonly referred to as the endophyte of tall fescue. Cattle grazing endophyte infected fescue have reduced body weight gains, reluctance to graze during periods of significant sunlight, heat and humidity and roughened haircoats at prominent signs of the condition.

Physiologically, the condition is characterized by a reduction in the serum prolactin concentration. Dopamine is the major inhibitor of pituitary prolactin secretion. The putative prolactin releasing factor seems to be serotonin. It has been hypothesized that the toxins elaborated from the endophyte act as dopaminergic agonists. Previous efforts to treat fescue toxicosis have included administration of compounds affecting dopamine and serotonin levels, including dopamine antagonists, serotonin agonists, and alpha$_2$-adrenergic agonists. A recent review of the neuroendocrine control mechanisms involved in fescue toxicosis is by Henson et al in *Domestic Animal Endocrinology*, 4(1), 7–15 (1987).

Bolt et al. was among the first to report, in *J. Amin. Sci.* 115, 48 (1982), that plasma prolactin levels in cattle grazing on fescue were reduced. (See also W. M. Hurley et al, *J. Animal Sci.* 51(2), 374–379 (1981)). He attempted to alleviate the symptoms of the fescue toxicosis using butyrophenone dopamine antagonists, specifically domperidone and spiperone (8-[4-fluorophenyl-4-oxobutyl]-1-phenyl-1, 3,8-triazospiro[4,5]decan-4-one), injected i.m. three times in two days at dosages of 15, 60, 240 mg or 2.5, 10 or 40 mg, respectively. His results indicated that while prolactin levels were increased in the drug treated animals, grazing time was not significantly increased by administration of the drug. He therefore concluded that additional mechanisms were involved in fescue toxicosis. As later reported by Henson (1987), administration of spiperone to sheep caused lethargy, disorientation, and loss in body weight due to lack of appetite.

Another drug, Clonidine (an alpha$_2$-adrenergic agonist used by Gorewit, *J. Endocrinol. Invest.* 4, 135–139 (1981), who found an increased serum prolactin concentration in cattle administered 2 micrograms of clonidine/kg of body weight, i.v. However, because of ruminant sensitivity to alpha$_2$-adrenergic stimulants, clonidine's potential as a therapeutic modality for fescue toxicosis at high dose levels is unfavorable.

Quipazine, a serotonin agonist, (2-(1-piperazinyl) quinoline maleate) was shown by Meltzer et al. *Life Sci.* 19, 1073–1078 (1976) to increase plasma prolactin concentrations in rats. Subsequently, Lipham, et al., in *Am. J. Vet. Res.*, 47 (5) 1089–1091 (May 1986), conducted a study using a synthetic ergot alkaloid CB-154 (2-bromoalphaergocryptine), given at 0.1 mg/kg of body weight, to suppress serum prolactin concentration in rats. Rats treated with this ergot compound were given other drugs (clonidine, quipazine, LY 53857, and combinations of these 3 drugs) to prevent suppression of serum prolactin concentrations or to increase serum prolactin concentrations.

A later study by Lipham et al in *Proc.Soc.Exper.Biol.Med.* 184,250-255(1987) reported on the effectiveness of quipazine and metoclopramide in protecting rats from CB-154 induced suppression of serum prolactin concentrations. The serum prolactin levels were shown to be most elevated using a combination of the two drugs. A quipazine-metoclopramide regimen was therefore suggested as having therapeutic potential for combating ergotlike fescue and other similar toxicities observed in cattle grazing on endophyte infected pasture grasses.

A comparison of the effects of metoclopramide and quipazine, alone or in combination, on prolactin levels in cattle was conducted as follows.

Pharmacologic modulation of prolactin (PRL) concentrations in yearling steers grazing bermuda grass pastures were undertaken utilizing the dopamine antagonist, metoclopramide monohydrochloride (MC), and the serotonin agonist quipazine maleate (Q). The objective was to determine whether these drugs had an effect on elevating serum PRL concentrations in steers with implications for alleviating fescue toxicosis. Dose-response relationships, routes of administration, and adverse side effects were examined.

Figure 2:
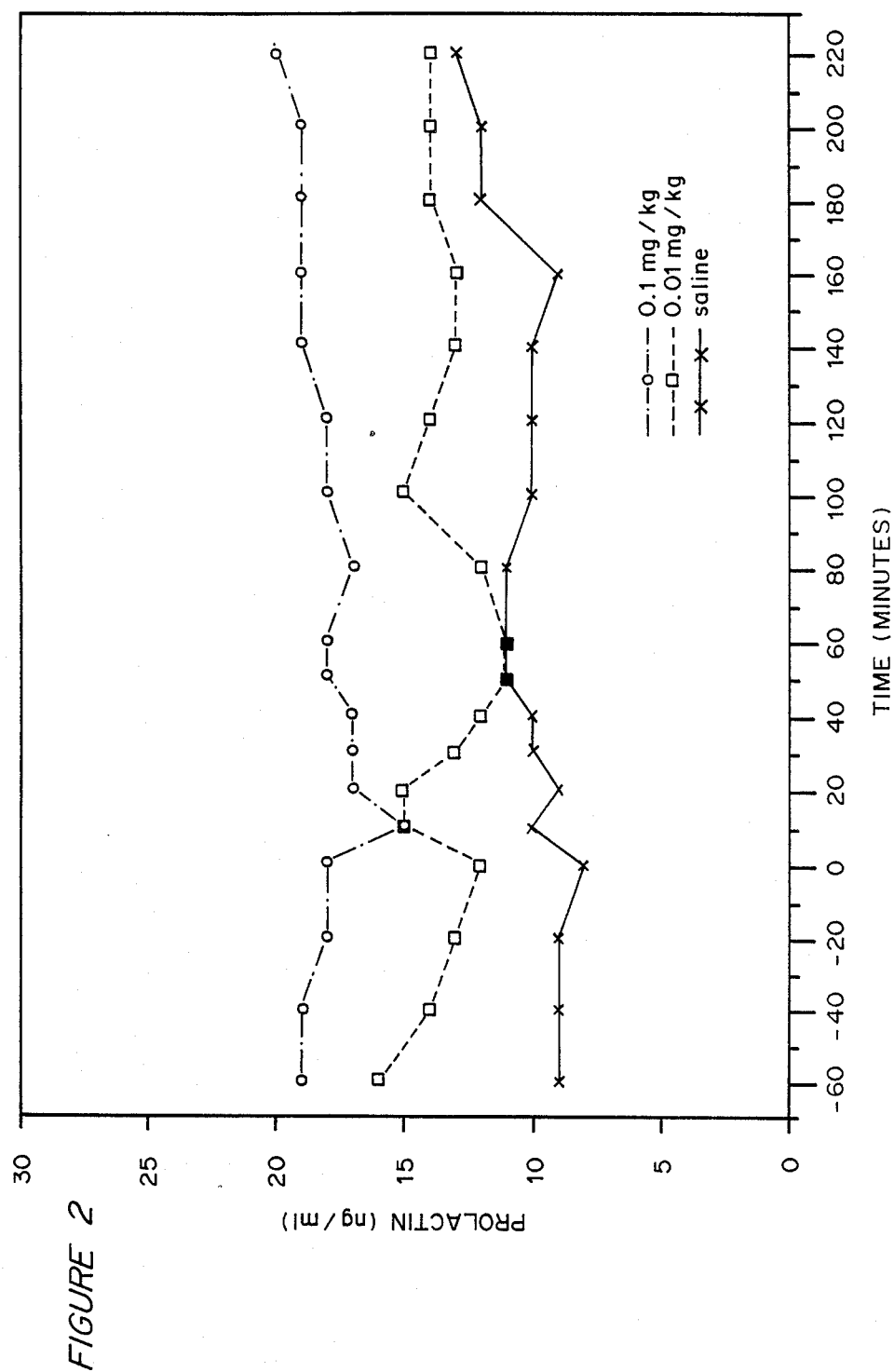
FIG. 2 is a graph of the effect of i.v. administration of quipazine maleate (0.01 and 0.1 mg/kg) on serum prolactin levels (ng/ml) over time (minutes) in cattle grazing on bermuda grass pasture.

In trial I, 20 steers were randomly assigned to: MC at 0.1 or 1.0 mg/kg; Q at 0.01 or 0.1 mg/kg; or saline (S), administered i.v. (n=4). Blood samples were obtained over time for serum PRL. MC at 1.0 mg/kg resulted in a numerically increased peak PRL (28.1 vs 9.6ng/ml, MC vs S, $p>0.05$) and PRL was numerically elevated by MC at 220 minutes post-injection, (22.1 vs 13.1 ng/ml, MC vs S) as shown in FIG. 1. Quipazine also produced elevated prolactin levels relative to the control, as shown in FIG. 2. Importantly, however, adverse behavioral effects (disorientation, aggressiveness) were noted in animals receiving Q.

Figure 3:
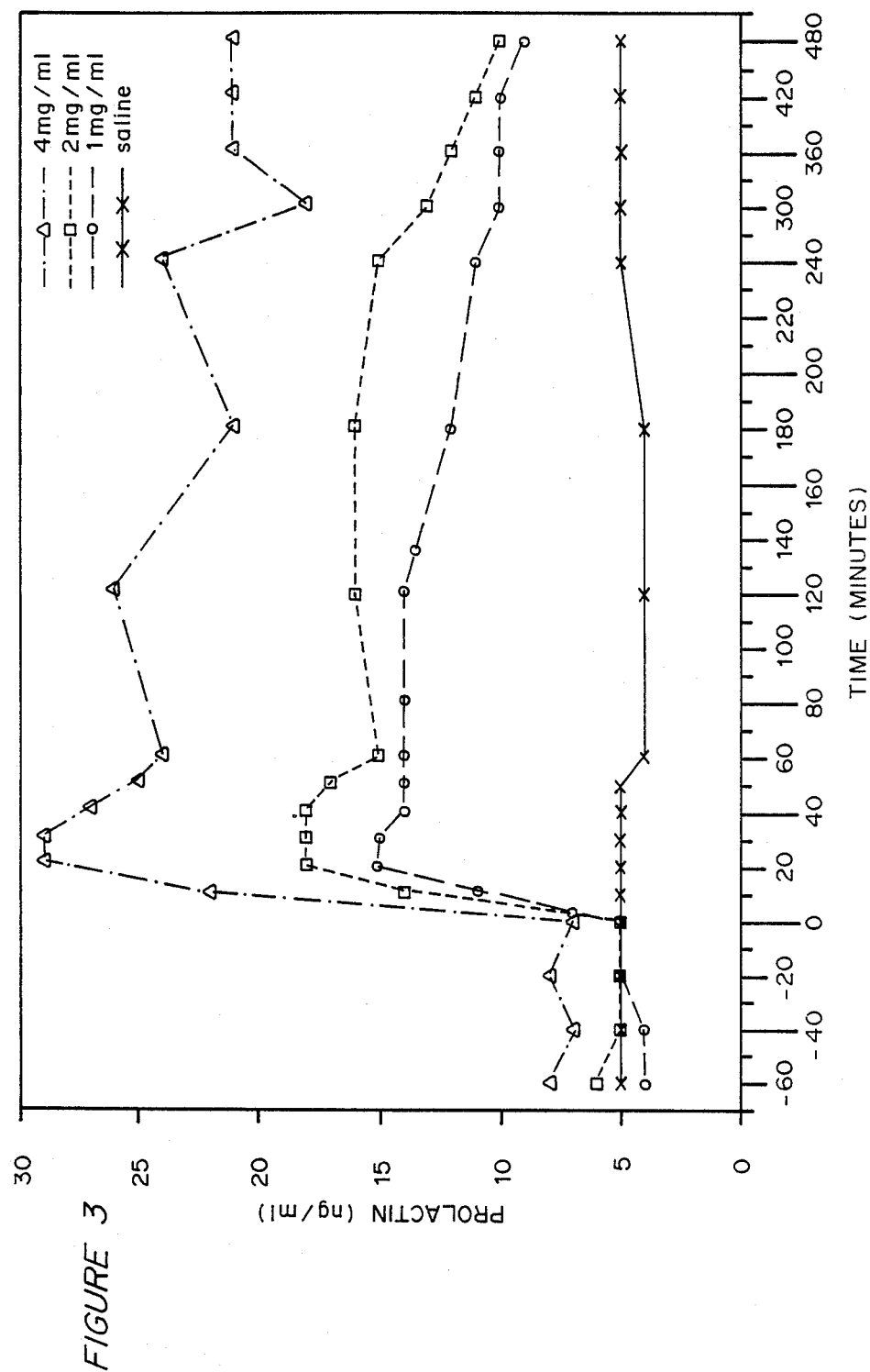
FIG. 3 is a graph of the effect of i.v. administration of metoclopramide (1, 2 and 4 mg/kg) on serum prolactin levels (ng/ml) over time (min) in cattle grazing on bermuda grass pasture.
Figure 4:
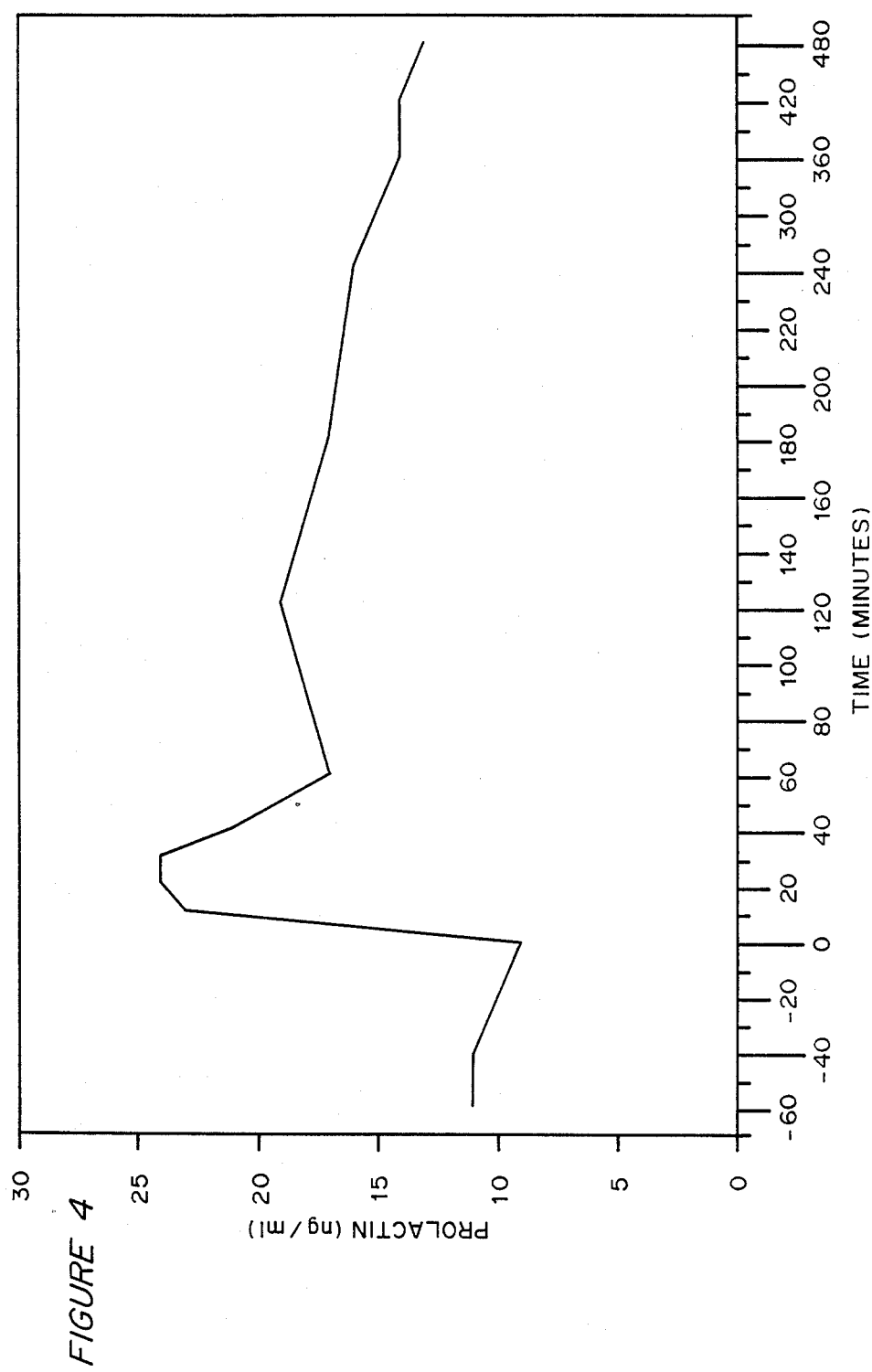
FIG. 4 is a graph of the effect of i.v. administration of metoclopramide (1.0 mg/kg) in combination with quipazine maleate (0.1 mg/kg) on serum prolactin levels (ng/ml) in cattle grazing on bermuda grass pasture.

In trial II, 20 steers received: 1.0 mg/kg MC and 0.1 mg/kg Q; 1.0, 2.0, or 4.0 mg/kg MC; or S by i.v. administration (n=4). The results are shown in FIG. 3 and FIG. 4. PRL was stimulated ($p<0.05$) for at least 480 minutes post injection.

In trial III, MC was given orally. Control steers received sucrose and treated steers received 25 g MC in gelatin capsules (n=8). Post treatment, steers receiving MC had elevated peak PRL (62.7 vs. 14.6 ng/ml, MC vs controls, $p<0.05$) at all intervals ($p<0.05$) until the termination of the experiment at 24 hours.

This study reemphasized the need for any useful method for treatment to take into account the behavioral as well as physiological effects of the drug. Potentially useful drugs must be screened for both using measurements of serum prolactin level in treated animals as well as observations of the behavioral effects, i.e , amount of grazing time, heat sensitivity, and presence of undesirable psychotic effects (disorientation, lack of appetite, lethargy).

On the basis of the favorable results using serum prolactin and immediate abnormal behavior as the test criteria, the substituted benzamide, metoclopramide, was further studied with respect to its effect on behavior and average daily weight gain (ADG) in grazing cattle.

Twenty-four yearling Angus steers were randomly assigned as pairs based on body weight to groups to examine the endocrine effects of low (approximately 25%) and high (approximately 60%) endophyte levels (percentage of the tillers examined with endophyte) and low (134 kg N.ha$^{-1}$·yr$^{-1}$) and high (336 kg N.ha$^{-1}$·yr$^{-1}$) nitrogen fertilization levels. These animals continuously grazed in 12, 0.7 ha paddocks along with other steers in a pt-and-take grazing system in order to maintain 1,800 kg dry matter/ha at all times. Three replicates of each group of endophyte level and N combination were made. The animals were weighed at 14 day intervals.

The animals were first allowed to graze the paddocks on Apr. 9, 1987. Beginning on May 7, 1987 one of the paired steers in each paddock was orally dosed Monday, Wednesday and Friday with metoclopramide (15 mg/kg) in a gelatin capsule and the other paired steer in each paddock was given a sucrose capsule as a control. Dosing continued for 10 weeks (May 8, 1987 until July 15, 1987). On selected days, jugular cannulae were inserted, filled with Na citrate, and protected by a neck wrap. Approximately 10 ml blood was drawn at 30 min. intervals for 2 ours. Thyrotropin-releasing hormone (TRH) dissolved in saline solution was then given i.v. at 33 micrograms/100 kg body weight with blood subsequently collected at 10-min intervals for 20 min. Administration of TRH acts directly on the pituitary to cause prolactin release, thereby serving as an internal control of pituitary competency. The blood was allowed to clot at ambient temperature, placed at 4° C. overnight, and centrifuged. The serum was harvested and stored frozen at −20° C. until analyzed via radioimmunoassay for prolactin (PRL) according to the method of Wallner, et al., *Amer. J. Vet. Res.* 44, 1317, 1322 (1983). All serum samples from a particular date were assayed together for PRL.

The results are shown in Tables I (prolactin data) and II (grazing and performance or weight gain data).

TABLE I

Mean basal prolactin (ng/ml) in metoclopramide treated steers grazing on toxic fescue

| Group | Pasture Treatment | Drug Treatment | Date Tested (5-28-87) | Ratio (M)/(C) | Date Tested (6-18-87) | Ratio (M)/(C) |
|---|---|---|---|---|---|---|
| I. | low endophyte high nitrogen | M | 65.83 | | 58.46 | |
| | | C | 9.68 | 6.80 | 32.00 | 1.83 |

TABLE I-continued

Mean basal prolactin (ng/ml) in metoclopramide treated steers grazing on toxic fescue

| Group | Pasture Treatment | Drug Treatment | Date Tested (5-28-87) | Ratio (M)/(C) | Date Tested (6-18-87) | Ratio (M)/(C) |
|---|---|---|---|---|---|---|
| II. | high endophyte low nitrogen | M C | 46.83 1.34 | 34.95 | 31.57 3.35 | 9.42 |
| III. | high endophyte high nitrogen | M C | 56.00 1.75 | 32.00 | 36.58 4.91 | 7.45 |
| IV. | low endophyte low nitrogen | M C | 69.51 8.81 | 7.89 | 51.42 16.32 | 3.15 |

M = metoclopramide treated (15 mg/kg orally Mon, Wed, Fri)
C = sucrose control
n = 3 steers/pasture treatment group, mean of four blood samples/steer

TABLE II

Percentage time spent grazing and Cumulative ADG (average daily gain) in lbs/day after 10 weeks of metoclopramide therapy in steers

| Group | Pasture Treatment | Drug Treatment | % time grazing* | ADG (lbs/day) |
|---|---|---|---|---|
| I. | low endophyte high nitrogen | M C | 27.22 1426 | .759 .531 |
| II. | high endophyte low nitrogen | M C | 14.49 0.79 | .684 .231 |
| III. | high endophyte high nitrogen | M C | 21.34 3.61 | .497 −.122 |
| IV. | low endophyte low nitrogen | M C | 26.71 5.88 | .827 .684 |

M = metoclopramide
C = sucrose control
*Observation on three days from 1200–1600 h
overall means (lbs/day):
M .691
C .331
metoclopramide treatment significant at p = .0005 (endophyte x metoclopramide interaction significant at p = 0049; i.e., the improvement in ADG was greater in steers grazing high endophyte than low endophyte infected tall fescue)

The results clearly establish that the metoclopramide treated animals are significantly (p=0.0005) more productive than the controls in terms of weight gains per day in pounds. The results also show that in drug treated animals, serum prolactin concentrations were increased by the treatment regimen of metoclopramide in comparison to their sucrose treated controls. The ratio of increase in PRL concentrations was from 1.83 to 34.95 times as great as the non-treated (sucrose) controls Further, in all instances, the metoclopramide treated animals spent more time grazing.

It is apparent from these studies including behavioral observations that the effect of the medication on the animal's behavior is an important factor to take into consideration. Drugs having psychotropic or neuroleptic side effects must be avoided. Alpha $_2$-adreneroic and serotonin agonists are therefore not generally useful in the treatment and prevention of fescue toxicosis in cattle. Domperidone, spiperone,.clonidine, and quipazine all have adverse behavioral effects which effectively eliminate them from use in the prevention or treatment of fescue toxicosis. This is not surprising since these compounds fall within the groups known to have neuroleptic effects that were originally developed for antipsychosis therapy, including phenothiazines, butyrophenones, and thioxanthenes. Pyrroloisoquinolines are another recently developed group of antipsychotics. All of these compounds having psychotropic effects are thought to be specific for $D_1$ receptors or a combination of $D_1$ and $D_2$ receptors.

At the present time, the preferred compounds are substituted benzamides such a metoclopramide (available from A. H. Robbins), sulpiride, tiapride, and alizapride. The substituted benzamides are believed to be specific for $D_2$ receptors. Since the ergot alkaloids are potent dopamine agonists, specifically at $D_2$ receptors, other dopamine antagonists specific for the $D_2$ receptors should be useful in a method for preventing or treating fescue toxicosis.

Although initial studies were done using i.v. injections or oral administration of a capsule three times a week, these are not the preferred modes of administration on a commercial scale. The drug can instead be administered by means of a time or slow release bolus, an implant, a component of a salt, mineral, protein or energy block or feed composition.

An example of a time release bolus is one presently used to deliver diflubenzuron to cattle for use in fly control (Vigilante ™, manufactured by Cyanamid, NJ). The bolus remains in the animals' rumen where it slowly digests over a period of months.

Biodegradable, biocompatible implants are presently in use for controlled drug delivery in humans and animals. Acceptable materials include cellulose, gelatin, polylactides, polyglycolides, polyanhydrides, polyorthoesters, polyethylene vinyl acetate, and other polymers which degrade by hydrolysis once implanted. The drug is encapsulated within the polymer using solvent casting or solution polymerization techniques. Excellent reviews of these materials are by Leong, et al. in J.

*Biomedical Material.Res.* 19, 941-955 (1985) and 20, 51-64 (1986).

Non-degradable implants such as one containing morantel tartrate (worm medication) sold as Paratect ™, by Pfizer Agricultural Division, NY, are also useful. Paratect ™ is packaged in a capsule made of a polyolefinic sleeve, a steel ring and a permeable polyethylene disc. Another non-degradable implant in commercial use is Synovex C ™, a progesterone-estradiol implant injected into the ear, manufactured by Syntex Agribusiness, Inc., West Des Moines, Iowa.

The drug can also be added to a salt or mineral block during casting, or mixed into feed. An example of a drug which is presently FDA approved for administration in controlled doses to free feeding cattle is Bovatec ™, manufactured by Hoffmann-LaRoche, Nutley, NJ, as described in *Beef*, 65-68 (October 1986). The drug can be mixed with feed or feed supplements, as with antibiotics such as Aureo S700 ™, manufactured by Cyanamid Animal Nutrition and Health Department, Wayne, NJ, and supplements such as Nutrena Beefcake Block, manufactured by Nutrena Feed Division, Cargill, Inc., Minneapolis, Minn or products of the Sifto Salt Division, Domtar Industries, Inc., Schiller Park, Ill.

The required dosage may vary according to the mode of administration and the size and type of animal being medicated. Different results may be achieved by providing a continuous release of compound over a sustained period of time from an implant or bolus than with discrete injections or oral administration. As noted earlier, 15 mg Metoclopramide/kg per day three times a week is a safe, effective dose in cattle.

Modifications and variations of the present invention, a method for prevention or treatment of fescue toxicosis, will be obvious to those skilled in the art from the foregoing detailed description of the invention. Such modifications and variations are intended to come within the scope of the appended claims.

We claim:

1. A method for treatment or prevention of fescue toxicosis comprising:
   administering a composition wherein the active agent consists of a dopamine antagonist at a pharmaceutically effective dosage to an animal, wherein said dopamine antagonist is selected from the group of $D_2$ specific antagonists having minimal neurological and psychological adverse effects in grazing animals.

2. The method of claim 1 wherein said dopamine antagonist is a substituted benzamide.

3. The method of claim 2 wherein said dopamine antagonist is selected from the group consisting of metoclopramide, sulpiride, tiapride, and alizapride.

4. The method of claim 2 wherein the dopamine antagonist is metoclopramide administered orally at a dosage of 15 mg/kg/day.

5. The method of claim 1 further comprising placing said dopamine antagonist in a pharmaceutically acceptable vehicle for injection.

6. The method of claim 1 further comprising encapsulating said dopamine antagonist in an implantable matrix.

7. The method of claim 5 further comprising administering the encapsulated dopamine antagonist at a release site.

8. The method of claim 1 further comprising mixing a pharmaceutically effective dose of said dopamine antagonist with a feed or feed supplement material.

* * * * *